(12) United States Patent
Schelling et al.

(10) Patent No.: US 10,383,177 B2
(45) Date of Patent: Aug. 13, 2019

(54) MICRO HEATING PLATE DEVICE AND SENSOR HAVING A MICRO HEATING PLATE DEVICE

(71) Applicant: Robert Bosch GmbH, Stuttgart (DE)

(72) Inventors: Christoph Schelling, Stuttgart (DE); Richard Fix, Weil im Schoenbuch (DE)

(73) Assignee: ROBERT BOSCH GMBH, Suttgart (DE)

( * ) Notice: Subject to any disclaimer, the term of this patent is extended or adjusted under 35 U.S.C. 154(b) by 816 days.

(21) Appl. No.: 14/917,708

(22) PCT Filed: Jul. 21, 2014

(86) PCT No.: PCT/EP2014/065589
§ 371 (c)(1),
(2) Date: Mar. 9, 2016

(87) PCT Pub. No.: WO2015/039786
PCT Pub. Date: Mar. 26, 2015

(65) Prior Publication Data
US 2016/0219649 A1 Jul. 28, 2016

(30) Foreign Application Priority Data
Sep. 19, 2013 (DE) .......................... 10 2013 218 840

(51) Int. Cl.
*H05B 3/26* (2006.01)
*G01N 27/12* (2006.01)
*H05B 3/66* (2006.01)

(52) U.S. Cl.
CPC ............. *H05B 3/26* (2013.01); *G01N 27/123* (2013.01); *G01N 27/128* (2013.01); *H05B 3/66* (2013.01)

(58) Field of Classification Search
CPC . H05B 3/26; H05B 3/66; H05B 3/262; H05B 3/265; H05B 3/267; H05B 3/28;
(Continued)

(56) References Cited

U.S. PATENT DOCUMENTS

| 4,703,555 A | 11/1987 | Hubner |
| 5,644,676 A * | 7/1997 | Blomberg ............... G01J 5/522 |
| | | 219/544 |

(Continued)

FOREIGN PATENT DOCUMENTS

| CN | 1297530 A | 5/2001 |
| CN | 101301992 A | 11/2008 |

(Continued)

OTHER PUBLICATIONS

Fonseca, et al. "Use of boron heavily doped silicon slabs for gas sensors based on free-standing membranes", J. Sensors and Actuators, B 130 (2008), pp. 538-545.

*Primary Examiner* — David J Walczak
(74) *Attorney, Agent, or Firm* — Norton Rose Fulbright US LLP; Gerard Messina

(57) ABSTRACT

A micro-hotplate apparatus including a diaphragm carrier device; a diaphragm that at least in part spans at least one cavity embodied in the diaphragm carrier device; and at least one heating conductor disposed on and/or in the diaphragm, the micro-hotplate apparatus additionally encompassing at least one reflector element that is disposed on an inner side, directed toward the cavity, of the diaphragm, in such a way that by way of the at least one reflector element a thermal radiation emitted from the at least one heating conductor and/or from the diaphragm is reflectable at least in part back onto and/or into the diaphragm. A sensor having a micro-hotplate apparatus is also described.

11 Claims, 3 Drawing Sheets

(58) Field of Classification Search
CPC .......... H05B 3/283; H05B 3/286; H05B 3/24; H05B 3/68; G01N 27/123; G01N 27/128
See application file for complete search history.

(56) References Cited

U.S. PATENT DOCUMENTS 8,859,303 B2 * 10/2014 Udrea .................... H05B 3/267
438/22
2004/0075140 A1  4/2004 Baltes et al.

FOREIGN PATENT DOCUMENTS

| | | |
|---|---|---|
| CN | 102050584 A | 5/2011 |
| DE | 4400838 A1 | 7/1995 |
| DE | 10 2007 057 500 A1 | 6/2009 |
| EP | 1104884 A2 | 6/2001 |
| JP | S 59-197848 | 11/1984 |
| JP | S60243549 A | 12/1985 |
| JP | H053895 B2 | 1/1993 |
| JP | H053896 B2 | 1/1993 |
| JP | H06201628 A | 7/1994 |
| JP | H08315969 A | 11/1996 |
| KR | 20090004279 | 1/2009 |
| WO | 2005/090958 A1 | 9/2005 |
| WO | 2008154693 A1 | 12/2008 |

* cited by examiner

MICRO HEATING PLATE DEVICE AND SENSOR HAVING A MICRO HEATING PLATE DEVICE

FIELD

The present invention relates to a micro-hotplate apparatus and to a sensor having a micro-hotplate apparatus.

BACKGROUND INFORMATION

German Patent Application No. DE 10 2007 057 500 A1 describes gas sensor elements. One of the gas sensor elements is a micromechanically manufactured metal oxide gas sensor that has a diaphragm which rests on a frame and carries a platinum heater. The frame is manufactured from a silicon wafer by way of an anisotropic etching process.

SUMMARY

The present invention relates to a micro-hotplate apparatus, and a sensor having a micro-hotplate apparatus.

The present invention implements a micro-hotplate apparatus, and a sensor equipped therewith, having a diminished heat delivery into an external environment of the micro-hotplate apparatus or of the sensor. Thanks to the reduction in heat delivery into the external environment, the efficiency of the micro-hotplate apparatus or of the sensor embodied therewith can be increased. Energy-saving operation of the micro-hotplate apparatus or of the sensor is thus possible. In addition, thanks to the diminution in heat delivery achievable by way of the present invention, the conventional risk of undesired heating or overheating of electronic components disposed close to the micro-hotplate apparatus or sensor is eliminated.

The micro-hotplate apparatus or the sensor equipped therewith can thus be disposed without difficulty in a comparatively small volume together with other (electronic) components, even with thermally sensitive components. This facilitates integration of the micro-hotplate apparatus or sensor, together with at least one other (electronic) component, in a comparatively small device, for example a mobile device (cell phone, watch) or in a sensor network (IoT). In addition, by way of the present invention thermal insulation elements that are conventionally necessary on a micro-hotplate apparatus or on a heated sensor can be simplified or omitted. In addition, devices equipped with the advantageous micro-hotplate apparatus or corresponding sensor can be made smaller or more space-saving by way of the present invention. The present invention furthermore also contributes to cheaper manufacturability of devices equipped with the micro-hotplate apparatus or sensor.

In an advantageous embodiment, the at least one reflector element is suspended on the inner side of the diaphragm. The at least one reflector element can thus be arranged in simple fashion at a comparatively short distance from the diaphragm.

In particular, an optical distance between the at least one reflector element and the at least one heating conductor, or an outer side, directed away from the cavity, of the diaphragm, can be equal to one-quarter of a wavelength at which the thermal radiation emitted from the at least one heating conductor and/or from the diaphragm exhibits an energy flux maximum (intensity maximum). This ensures advantageous reabsorption, by the diaphragm, of the thermal radiation reflected by way of the at least one reflector element.

As an alternative or supplement thereto, the at least one reflector element or at least one further reflector element can be embodied on a rear side, directed away from the diaphragm, of the cavity. Equipping the micro-hotplate apparatus with at least one reflector element or further reflector element disposed in this manner also ensures the advantageous reduction of an undesired heat delivery into the external environment of the micro-hotplate apparatus.

For example, the diaphragm carrier device can encompass a substrate by way of which the cavity is structured, the substrate being fastened by way of a bonding or adhesive connection, on a carrier plate on which the at least one reflector element or the at least one further reflector element is disposed, in such a way that the at least one reflector element or the at least one further reflector element is located on the rear side of the cavity. A micro-hotplate apparatus embodied in this fashion can be manufactured comparatively simply and relatively inexpensively.

In a further advantageous embodiment, at least one front reflector element is disposed on the outer side of the diaphragm. This can also be referred to as a disposition of the at least one front reflector element oppositely to the outer side of the diaphragm. The undesired delivery of thermal energy to an external environment of the micro-hotplate apparatus can be suppressed or diminished by way of the at least one front reflector element as well.

In addition, the at least one reflector element, the at least one further reflector element, and/or the at least one front reflector element can have an elliptical or paraboloid shape. Preferably the elliptical or paraboloid shape is designed so that its focal point coincides with a plane of the diaphragm. This increases the effectiveness of the at least one reflector element, the at least one further reflector element, and/or the at least one front reflector element.

In a further advantageous embodiment the diaphragm has patterns of plasmonic structures. A thermal emission, in particular a thermal emission outside a resonance wavelength, can be suppressed by way of the plasmonic structures. In addition, the plasmonic structures of the diaphragm ensure efficient reabsorption of the thermal radiation reflected back onto the diaphragm, in particular around its resonance wavelength.

As a supplement or alternative thereto, the at least one reflector element can also have a pattern of plasmonic structures. Plasmonic structures can thus also be used to increase the effectiveness of the at least one reflector element, of the at least one further reflector element, and/or of the at least one front reflector element.

The micro-hotplate apparatus can be embodied, for example, as a sensor component for a sensor and can encompass, on and/or in the diaphragm, at least one sensitive material that exhibits at least one physical magnitude that is dependent on a substance concentration of at least one substance. The micro-hotplate apparatus can thus contribute to the implementation of an advantageous gas sensor, particle sensor, and/or liquid sensor. It is noted, however, that the usability of the micro-hotplate apparatus is not limited to a sensor component for a sensor, in particular to the sensor types enumerated here.

The above-described advantages of the micro-hotplate apparatus are also ensured in the context of a sensor having such a micro-hotplate apparatus. The micro-hotplate apparatus enables advantageous integration of substance-sensitive sensor components into consumer electronics, mobile sensors, and/or sensor networks. Miniaturization of these devices having the integrated micro-hotplate apparatus is enhanced by way of the present invention. In addition, there is no risk that heating of the micro-hotplate apparatus will have a negative effect on other components or sensors in the same package and/or in the same device.

BRIEF DESCRIPTION OF THE DRAWINGS

Further features and advantages of the present invention will be explained below with reference to the figures.

DETAILED DESCRIPTION OF EXAMPLE EMBODIMENTS

Figure 1A:
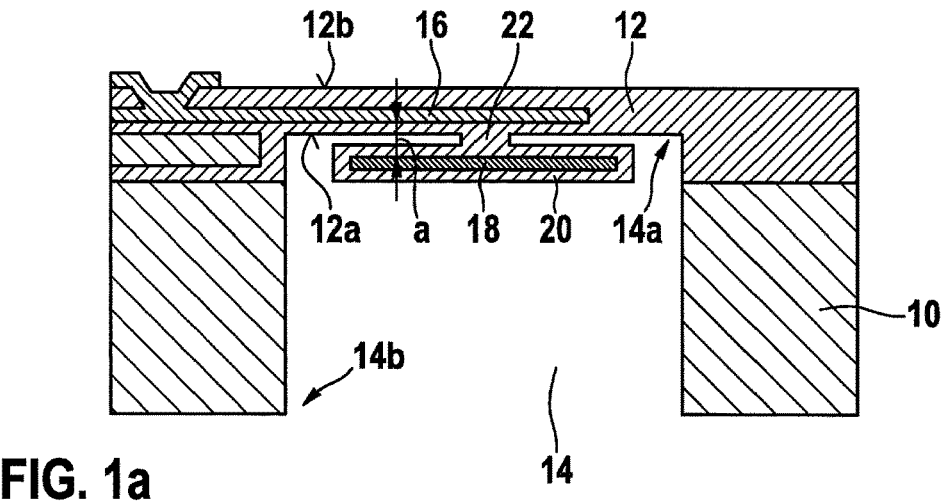
FIGS. 1a and 1b show a cross section and a plan view of a first embodiment of the micro-hotplate apparatus.
Figure 1B:
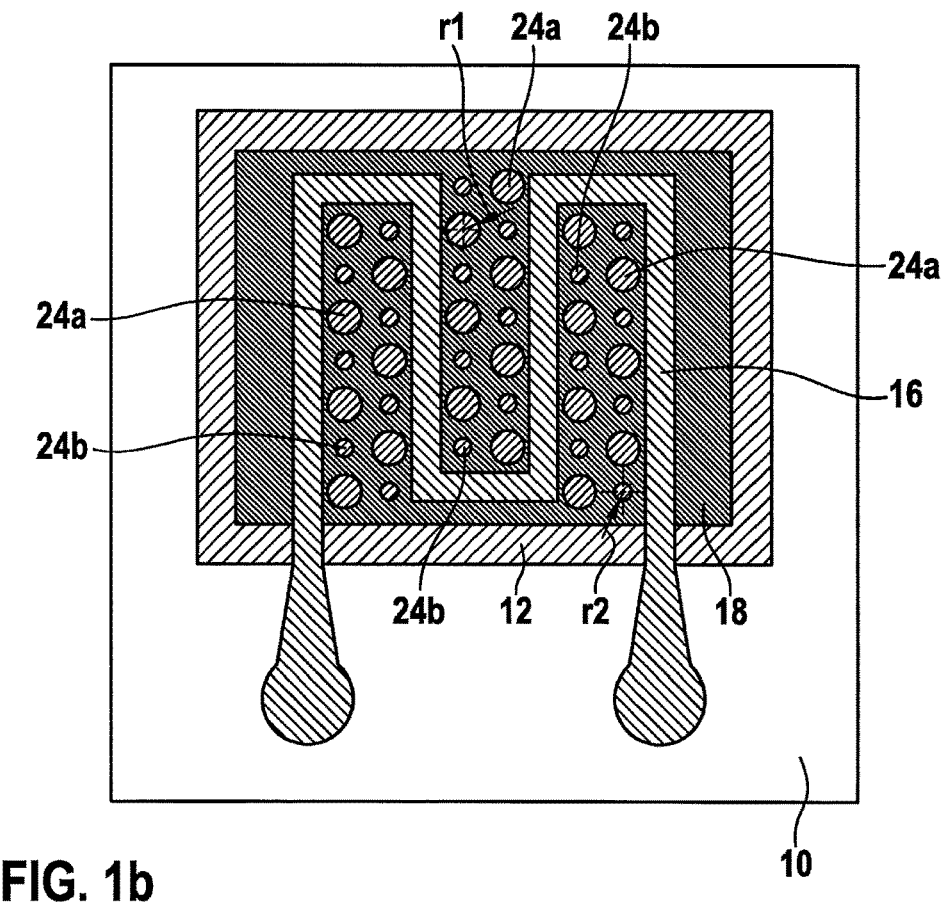

FIGS. 1a and 1b show a cross section and a plan view of a first embodiment of the micro-hotplate apparatus.

The micro-hotplate apparatus schematically depicted in FIGS. 1a and 1b encompasses a diaphragm carrier device 10 and a diaphragm 12 that at least partly spans a cavity 14 embodied in diaphragm carrier device 10. In particular, a diaphragm side 14a of cavity 14 can be completely covered by diaphragm 12. Diaphragm carrier device 10 can encompass or be, for example, a substrate by way of which cavity 14 is structured. For example, a semiconductor substrate, such as in particular a silicon substrate, can advantageously be used to manufacture diaphragm carrier device 10 having cavity 14 embodied therein. It is noted, however, that the possible embodiment described here for implementing diaphragm carrier device 10 is merely exemplary.

Diaphragm 12 can be of single-layer or multi-layer construction. Diaphragm 12 can be embodied in particular as dielectric diaphragm 12. Diaphragm 12 encompasses, for example, silicon oxide or silicon nitride. Instead of the materials recited here, however, others can also be used to manufacture diaphragm 12.

The micro-hotplate apparatus also has at least one heating conductor 16 disposed on and/or in diaphragm 12. The at least one heating conductor 16 can be embodied in particular as a heating element integrated into diaphragm 12. The at least one heating conductor 16 can be embodied, for example, in a meander shape. Platinum and/or nickel can be utilized to manufacture the at least one heating conductor 16.

The micro-hotplate apparatus also has at least one reflector element 18 that is disposed on an inner side 12a, directed toward cavity 14, of diaphragm 12 in such a way that a thermal radiation emitted from the at least one heating conductor 16 and/or from diaphragm 12 is at least in part reflectable by way of the at least one reflector element 18 back onto and/or into diaphragm 12. As long as a temperature of diaphragm 12 and/or of the at least one heating conductor 16 is higher than a temperature of the at least one reflector element 18, a portion of the thermal radiation can be reflected by way of the at least one reflector 18 back into diaphragm 12, and is thus not lost. The at least one reflector element 18 thus effects a reduction in the power consumption of the micro-hotplate apparatus. The energy consumption of the micro-hotplate apparatus can thus be limited. Undesired heating of an external environment of the micro-hotplate apparatus can furthermore be counteracted by way of the at least one reflector element 18. Even thermally sensitive elements can therefore be disposed closer to the micro-hotplate apparatus without requiring (more complex) thermal insulation of the micro-hotplate apparatus with respect to its external environment. The decreased heat delivery of the micro-hotplate apparatus of FIGS. 1a and 1b to its external environment also ensures less stress on thermally sensitive elements disposed close to it, which improves their robustness and lengthens their service life. The advantageous equipping of the micro-hotplate apparatus with the at least one reflector element 18 also enables inexpensive integration of the micro-hotplate apparatus, together with other electronic components, into a comparatively small device, for example a mobile device.

The at least one reflector element 18 can be constituted at least in part from a metal. Silver and/or gold can be used, for example, for the at least one reflector element 18. The at least one reflector element 18 can be of single- or multi-layer construction.

In the embodiment of FIGS. 1a and 1b, the at least one reflector element 18 is suspended on inner side 12a of diaphragm 12. The at least one reflector element 18 can thus be referred to as a reflector shield and/or absorber shield. The at least one reflector element 18 can be connected in spot fashion to diaphragm 12. In particular, a centered connection can be embodied between the at least one reflector element 18 and diaphragm 12.

The suspension, depicted in FIG. 1a, of the at least one reflector element 18 on inner side 12a of diaphragm 12 is implementable, for example, by the fact that the at least one reflector element 18 is embedded into a (preferably dielectric) material 20 that has at least one protrusion 22 contacting inner side 12a of diaphragm 12. In particular, the at least one material of diaphragm 12 can be used to embed the at least one reflector element 18 and to form the at least one protrusion 22. Easily executable etching and deposition steps can thus be executed in order to create the suspension of the at least one reflector element 18. The micro-hotplate apparatus depicted in FIGS. 1a and 1b can thus be manufactured inexpensively. In addition, a design specification can still be reliably adhered to even in a context of mass-produced manufacture of the micro-hotplate apparatus.

The intensity maximum of an emitted thermal radiation of a black-body radiator is obtained in accordance with equation (eq. 1), based on Wien's displacement law, as:

$$\nu_{max} = ((2.82 * k_B)/h) * T, \quad \text{(eq. 1)}$$

where $\nu_{max}$ is the frequency at which the thermal radiation emitted from the at least one heating conductor 16 and/or from diaphragm 12 has an intensity maximum. T is the temperature, $k_B$ the Boltzmann constant, and h is Planck's constant.

Temperatures T that are between 150° C. and 700° C. are often achieved by way of the at least one heating conductor 16. This results in an intensity maximum of the emitted thermal radiation in a wavelength range from 5 μm to 12 μm. The spectrum of the emitted thermal radiation is generally relatively broad-band. The indications and numerical values presented here, however, are merely exemplary.

Preferably, an optical distance a between the at least one reflector element 18 and the at least one heating conductor 16, or an outer side 12b, directed away from cavity 14, of diaphragm 12, is equal to one-quarter of a wavelength at which the thermal radiation emitted from the at least one heating conductor 16 and/or from diaphragm 12 exhibits an energy flux maximum (intensity maximum). This increases the efficiency of the at least one reflector element 18 as a reflector shield and/or absorber shield. For example, the thermal energy can thereby be reflected back in controlled fashion onto the at least one heating conductor 16 or at least onto a material (to be heated) disposed on outer side 12b of diaphragm 12.

The "optical distance" a can be understood as a magnitude in accordance with equation (eq. 2), where:

$$a = \Sigma d_i * n_i,\qquad(\text{eq. 2})$$

where $d_i$ denotes the layer thicknesses of the layers located between the at least one reflector element 18 and the at least one heating conductor 16 or outer side 12b of diaphragm 12, and $n_i$ denotes the refractive indices of these layers.

As a supplement or alternative to the at least one reflector element 18, the micro-hotplate apparatus can also encompass at least one front reflector element disposed on outer side 12b of diaphragm 12 and/or at least one further reflector element embodied on a rear side 14b, directed away from diaphragm 12, of cavity 14. Reference is made to embodiments described below regarding possible configurations for the at least one front reflector element or the at least one further reflector element.

As is evident from FIG. 1b, diaphragm 12 has patterns of plasmonic structures 24a and 24b. The patterns of plasmonic structures 24a and 24b can also be referred to as "plasmonic absorber structures." Electromagnetic (thermal) radiation can excite collective oscillations of the electron cloud, called "plasmons," in plasmonic structures 24a and 24b. The excited plasmons result, via scattering mechanisms, in a heating of diaphragm 12. The patterns of plasmonic structures 24a and 24b thus bring about a suppression of the thermal radiation emitted from diaphragm 12 and improve reabsorption, in diaphragm 12, of the thermal radiation reflected back from the at least one reflector element 18.

Plasmonic structures 24a and 24b are preferably made from metal. Plasmonic structures 24a and 24b can be, for example, (metallic) prisms, in particular having a circular, elliptical, and/or cross-shaped base surface. Inverse structures, for example missing prisms, can also be embodied in a continuous metal layer as plasmonic structures 24a and 24b. Plasmonic structures 24a and 24b can be paraphrased in particular as "lattice structures."

At an intensity maximum of the emitted thermal radiation in a wavelength region from 5 μm to 12 μm, patterns of plasmonic structures 24a to 24b in which a distance between adjacent plasmonic structures 24a and 24b is between 0.5 μm and 10 μm are advantageous. Advantageously, a structure size of a plasmonic structure 24a or 24b, for example a (maximum) width of a plasmonic structure 24a or 24b or a radius r1 or r2 of a circular base area of a plasmonic structure 24a or 24b, is between 0.1 μm and 5 μm. The numerical values presented here are, however, merely exemplary.

A diaphragm 12 can have, for example, a pattern of uniformly shaped plasmonic structures 24a and 24b. Preferably, however, diaphragm 12 has a pattern of plasmonic structures 24a and 24b that encompasses at least plasmonic structures 24a having a first structure size or a first radius r1, and plasmonic structures 24b having a second structure size or a second radius r2 (not equal to the first structure size or first radius r1). This allows a bandwidth of an emission spectrum or absorption spectrum of the pattern of plasmonic structures 24a and 24b to be increased.

The at least one structure size of plasmonic structures 24a and 24b can be adjusted to at least one desired value in simple fashion. A thermal emission of diaphragm 12, especially outside its resonance wavelength, can thereby be suppressed. Provision can also reliably be made for efficient reabsorption of the back-reflected thermal radiation close to its resonance wavelength.

In an advantageous refinement the at least one reflector element 18 can also have a pattern of plasmonic structures. An absorption behavior of the at least one reflector element 18 can be improved by way of the plasmonic structures. The respective reflector element 18 embodied with the plasmonic structures thus heats up as a result of the emitted thermal radiation, and delivers the thermal energy back to diaphragm 12 by thermal conduction via protrusion 22. The at least one reflector element 18 can thus perform the function of an energy buffer.

The plasmonic structures of reflector element 18 also can be metallic structures, such as in particular (metallic) prisms (having a circular, elliptical, and/or cross-shaped base surface), inverse structures (e.g. missing prisms), and/or (metallic) grid structures. In this case as well, a distance between adjacent plasmonic structures can be between 0.5 μm and 10 μm, and a structure size, for example a (maximum) width or a radius, can be between 0.1 μm and 5 μm. The plasmonic structures can thus also be coordinated with an energy emission maximum of the thermal radiation. A pattern of identically shaped plasmonic structures, or of plasmonic structures 24a and 24b having at least two different structure sizes or radii, can selectably be embodied.

Figure 2:
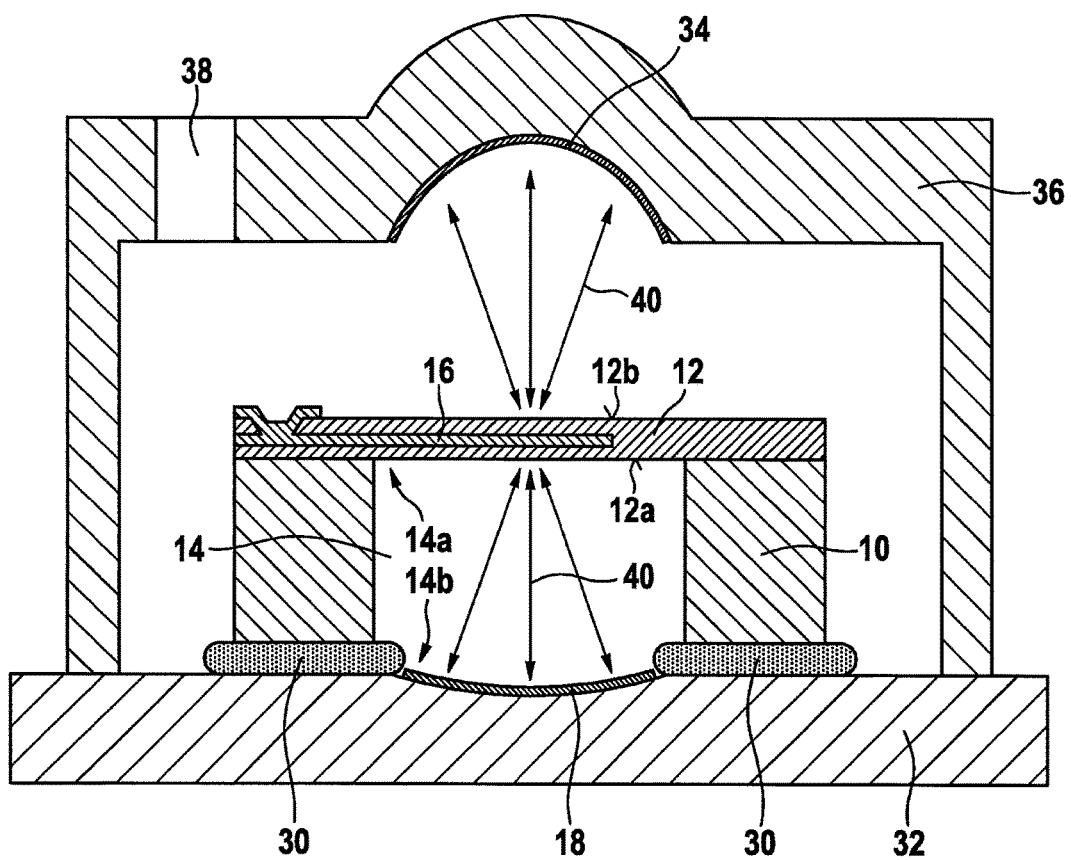
FIG. 2 schematically depicts a second embodiment of the micro-hotplate apparatus.

FIG. 2 schematically depicts a second embodiment of the micro-hotplate apparatus.

In the micro-hotplate apparatus schematically depicted in FIG. 2, the at least one reflector element 18 is embodied on a rear side 14b, directed away from diaphragm 12, of cavity 14. For this purpose the substrate of diaphragm carrier device 10 is fastened, by way of a bonding or adhesive connection 30, to a carrier plate 32 on which the at least one reflector element 18 is disposed, in such a way that the at least one reflector element 18 is located on rear side 14b of the cavity.

The micro-hotplate apparatus of FIG. 2 also has at least one front reflector element 34 on an outer side 12b, directed away from cavity 14, of diaphragm 12. The at least one front reflector element 34 is embodied, by way of example, on an inner side of a cap 36, cap 36 being fastened on carrier plate 32. Carrier plate 32 and cap 36 can additionally be used as a housing of the micro-hotplate apparatus. The housing can be embodied selectably to be liquid-tight, air-tight, or to have at least one housing opening 38. It is thus possible to equip the micro-hotplate apparatus with reflector elements 18 and 34 simultaneously with a packaging of diaphragm 12 in a housing. The number of method steps to be executed in order to manufacture the micro-hotplate apparatus of FIG. 2 can thus be reduced.

Because the micro-hotplate apparatus is equipped with several reflector elements 18 and 34, a comparatively large amount of the emitted thermal radiation can be reflected back onto diaphragm 12. In particular, due to a curved embodiment of the at least one reflector element 18 and/or of the at least one front reflector element 34, thermal radiation can be collected from a larger solid angle and reflected.

Preferably, the at least one reflector element 18 and/or the at least one front reflector 34 are embodied with an elliptical or paraboloid shape. In particular, a focal point of the respective ellipse or paraboloid can coincide with a plane of diaphragm 12. As depicted by way of arrows 40 in FIG. 2, the back-reflected thermal radiation can in that manner be directed in targeted fashion onto a specific region of diaphragm 12. This is advantageous in particular if a comparatively high temperature is desired only at a specific region of diaphragm 12.

Figure 3:
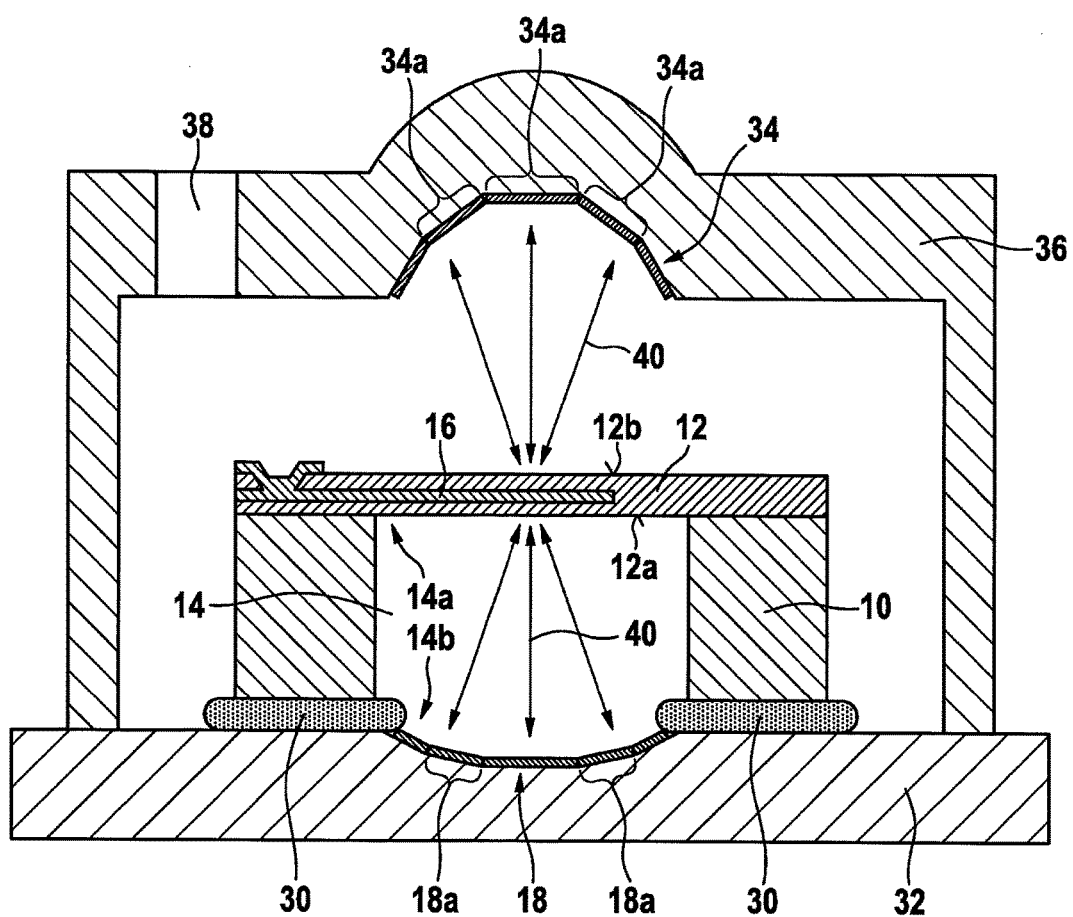
FIG. 3 schematically depicts a third embodiment of the micro-hotplate apparatus.

FIG. 3 schematically depicts a third embodiment of the micro-hotplate apparatus.

The micro-hotplate apparatus schematically depicted in FIG. 3 has all the components of the embodiment previously described. Instead of a single-surface embodiment of reflector element 18 and of front reflector element 34, however, the micro-hotplate apparatus of FIG. 3 has, respectively for elements 18 and 34, several planar reflector surfaces 18a and 34a that, when assembled, simulate an ellipsoidal or paraboloid shape for each of elements 18 and 34. The preferred embodiment of elements 18 and 34 is thus possible even without performing complex manufacturing methods.

All the above micro-hotplate apparatuses can be used as sensor components for a sensor. For this, at least one sensitive material that exhibits at least one physical magnitude that is dependent on a substance concentration of at least one substance can be deposited on and/or in diaphragm 12. A sensor component embodied in this fashion can be used, for example, for a gas sensor, particle sensor, and/or liquid sensor. An evaluation of the sensor component can be accomplished, for example, by way of a measurement of a change, attributable to the substance concentration of the at least one substance, in the physical magnitude, for example in an electrical conductivity (resistive), a capacitance (capacitive), and/or an emission work (field effect-based).

A suitable sensitive material is, for example, $SnO_2$ and/or $WO_3$. A micro-hotplate apparatus used as a sensor component can, however, also have a different sensitive material.

In order to improve sensitivity and/or regeneration, the micro-hotplate apparatus can be heated by way of the at least one heating conductor 16 to a desired temperature, for example in a temperature range between 150° C. and 700° C. The at least one heating conductor 16 can be energized, for example, in pulsed fashion. With such pulsed operation of the micro-hotplate apparatus it can reliably be assumed that a temperature of the at least one heating conductor 16 and/or of diaphragm 12 is higher than a temperature of the at least one reflector element 18.

What is claimed is:

1. A micro-hotplate apparatus comprising:
   a diaphragm carrier device;
   a diaphragm that at least in part spans at least one cavity in the diaphragm carrier device;
   at least one heating conductor disposed one of on or in the diaphragm; and
   at least one reflector element disposed on an inner side, directed toward the cavity, of the diaphragm, in such a way that by way of the at least one reflector element a thermal radiation, emitted at least one of: i) from the at least one heating conductor, and ii) from the diaphragm, is reflectable at least in part back at least one of onto and into the diaphragm;
   wherein the diaphragm has patterns of plasmonic structures.

2. The micro-hotplate apparatus as recited in claim 1, wherein the at least one reflector element is suspended on the inner side of the diaphragm.

3. The micro-hotplate apparatus as recited in claim 1, wherein an optical distance between the at least one reflector element and the at least one heating conductor, or an outer side, directed away from the cavity, of the diaphragm, is equal to one-quarter of a wavelength at which the thermal radiation emitted from the at least one of at least one heating conductor, and from the diaphragm exhibits an energy flux maximum.

4. The micro-hotplate apparatus as recited in claim 1, wherein the at least one reflector element or at least one further reflector element is embodied on a rear side, directed away from the diaphragm, of the cavity.

5. The micro-hotplate apparatus as recited in claim 4, wherein the diaphragm carrier device is a substrate by way of which the cavity is structured, and the substrate being fastened, by way of a bonding or adhesive connection, on a carrier plate on which the at least one reflector element or the at least one further reflector element is disposed, in such a way that the at least one reflector element or the at least one further reflector element is located on the rear side of the cavity.

6. The micro-hotplate apparatus as recited in claim 1, wherein at least one front reflector element is disposed on an outer side of the diaphragm.

7. The micro-hotplate apparatus as recited in claim 6, wherein at least one of the at least one reflector element, and the at least one front reflector element, has an elliptical or paraboloid shape.

8. The micro-hotplate apparatus as recited in claim 1, wherein the micro-hotplate apparatus is embodied as a sensor component for a sensor and includes, at least one of on and in the diaphragm, at least one sensitive material that exhibits at least one physical magnitude that is dependent on a substance concentration of at least one substance.

9. A micro-hotplate apparatus, comprising:
   a diaphragm carrier device;
   a diaphragm that at least in part spans at least one cavity in the diaphragm carrier device;
   at least one heating conductor disposed one of on or in the diaphragm; and
   at least one reflector element disposed on an inner side, directed toward the cavity, of the diaphragm, in such a way that by way of the at least one reflector element a thermal radiation, emitted at least one of: i) from the at least one heating conductor, and ii) from the diaphragm, is reflectable at least in part back at least one of onto and into the diaphragm;
   wherein the at least one reflector element has at least one pattern of plasmonic structures.

10. A sensor having a micro-hotplate apparatus, the micro-hotplate apparatus comprising:
    a diaphragm carrier device;
    a diaphragm that at least in part spans at least one cavity in the diaphragm carrier device;
    at least one heating conductor disposed one of on or in the diaphragm; and
    at least one reflector element disposed on an inner side, directed toward the cavity, of the diaphragm, in such a way that by way of the at least one reflector element a thermal radiation, emitted at least one of: i) from the at least one heating conductor, and ii) from the diaphragm, is reflectable at least in part back at least one of onto and into the diaphragm;
    wherein the diaphragm has patterns of plasmonic structures.

11. A sensor having a micro-hotplate apparatus, the micro-hotplate apparatus comprising:
    a diaphragm carrier device;
    a diaphragm that at least in part spans at least one cavity in the diaphragm carrier device;
    at least one heating conductor disposed one of on or in the diaphragm; and
    at least one reflector element disposed on an inner side, directed toward the cavity, of the diaphragm, in such a way that by way of the at least one reflector element a thermal radiation, emitted at least one of: i) from the at least one heating conductor, and ii) from the diaphragm, is reflectable at least in part back at least one of onto and into the diaphragm;
wherein the at least one reflector element has at least one pattern of plasmonic structures.

* * * * *